US010966621B2

(12) United States Patent
Han

(10) Patent No.: US 10,966,621 B2
(45) Date of Patent: Apr. 6, 2021

(54) FLEXIBLE NEURAL PROBES

(71) Applicant: INTERNATIONAL BUSINESS MACHINES CORPORATION, Armonk, NY (US)

(72) Inventor: Shu-Jen Han, Cortlandt Manor, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 430 days.

(21) Appl. No.: 15/616,985

(22) Filed: Jun. 8, 2017

(65) Prior Publication Data

US 2018/0078194 A1 Mar. 22, 2018

Related U.S. Application Data

(62) Division of application No. 15/268,020, filed on Sep. 16, 2016, now Pat. No. 10,588,526.

(51) Int. Cl.
*A61B 5/04* (2006.01)
*A61B 5/0478* (2006.01)
*A61B 5/00* (2006.01)
A61B 5/145 (2006.01)

(52) U.S. Cl.
CPC ........ *A61B 5/04001* (2013.01); *A61B 5/0478* (2013.01); *A61B 5/4064* (2013.01); *A61B 5/6868* (2013.01); *A61B 5/14503* (2013.01); *A61B 5/14539* (2013.01); *A61B 2560/063* (2013.01); *A61B 2562/028* (2013.01);
(Continued)

(58) Field of Classification Search
CPC .................................................. A61B 5/04001
See application file for complete search history.

(56) References Cited

U.S. PATENT DOCUMENTS

| 6,304,784 B1 | 10/2001 | Allee et al. |
| 7,689,260 B2 | 3/2010 | Finch et al. |
| 8,229,539 B1 | 7/2012 | Motoyoshi et al. |

(Continued)

FOREIGN PATENT DOCUMENTS

| FR | 2955260 | 7/2011 |
| WO | 2015153958 A1 | 10/2015 |

OTHER PUBLICATIONS

Ji et al; "An Implantable CMOS Circuit Interface for Multiplexed Microelectrode Recording Arrays," IEEE Journal of Solid-State Circuits, vol. 27, No. 3, Mar. 1992, pp. 433-443.
(Continued)

*Primary Examiner* — Livius R. Cazan
(74) *Attorney, Agent, or Firm* — Cantor Colburn LLP; Randall Bluestone

(57) ABSTRACT

Embodiments include microelectrodes including a flexible shank and a bioabsorbable material surrounding the flexible shank. The flexible shank can include a flexible substrate, a circuit, and a plurality of sensors. Embodiments also include a methods of forming flexible active electrode arrays including depositing a flexible polymer on a substrate. The methods also include forming a plurality of sensors on the flexible polymer and attaching a silicon-based chip to the flexible shank. The methods also include coating the flexible shank in a bioabsorbable material and cutting the shank and a portion of the bioabsorbable material from the substrate.

15 Claims, 10 Drawing Sheets

(52) U.S. Cl.
CPC ............ *A61B 2562/0209* (2013.01); *A61B 2562/0285* (2013.01); *A61B 2562/166* (2013.01)

(56) References Cited

U.S. PATENT DOCUMENTS

| | | | |
|---|---|---|---|
| 8,428,732 | B2 | 4/2013 | Nishida et al. |
| 9,114,004 | B2 | 8/2015 | Fan |
| 2003/0100823 | A1 | 5/2003 | Kipke et al. |
| 2006/0173263 | A1 | 8/2006 | He et al. |
| 2007/0167815 | A1 | 7/2007 | Jacobsen et al. |
| 2007/0211711 | A1 | 9/2007 | Clayton |
| 2007/0265543 | A1 | 11/2007 | Vansickle et al. |
| 2008/0283875 | A1 | 11/2008 | Mukasa |
| 2009/0118805 | A1 | 5/2009 | Greenberg et al. |
| 2010/0106041 | A1 | 4/2010 | Ghovanloo et al. |
| 2011/0138938 | A1 | 6/2011 | Giszter |
| 2011/0144471 | A1 | 6/2011 | Hsu et al. |
| 2012/0123318 | A1* | 5/2012 | Ek .................. A61B 5/04001 604/20 |
| 2012/0226130 | A1 | 9/2012 | Graff et al. |
| 2013/0006147 | A1 | 1/2013 | Fukuda |
| 2013/0085359 | A1 | 4/2013 | Yao et al. |
| 2013/0238129 | A1 | 9/2013 | Rosa et al. |
| 2013/0338744 | A1 | 12/2013 | Frewin et al. |
| 2014/0206975 | A1 | 7/2014 | Lang |
| 2014/0288458 | A1* | 9/2014 | Yoon .................. A61N 1/0529 600/547 |
| 2014/0378993 | A1 | 12/2014 | Shah et al. |
| 2016/0007874 | A1 | 1/2016 | Ma et al. |
| 2016/0128589 | A1 | 5/2016 | Tabib-Azar |

OTHER PUBLICATIONS

List of IBM Patents or Patent Applications Treated as Related: (Appendix P) Date Filed: Jun. 9, 2017; 2 pages.
U.S. Appl. No. 15/268,020, filed Sep. 16, 2016; Entitled: Flexible Neural Probes.
U.S. Appl. No. 15/474,198, filed Mar. 30, 2017; Entitled: Flexible Neural Probes.
Berdondini et al., Active pixel sensor array for high spatio-temporal resolution electrophysiological recordings from single cell to large scale neuronal networks, 2009, Lab Chip, 9, 2644-2651. Retrieved on Jan. 17, 2019 from http://pubs.rsc.org/en/Content/ArticleLanding/2009/LC/b907394a#!divAbstract.
Seo et al., Fabrication and electrical properties of single wall carbon nanotube channel and graphene electrode based transistors array, 2015, Appl Phys Letter, 107, 033103. Retrieved on Jan. 17, 2018 from http://aip.scitation.org/doi/full/10.1063/1.4927054.
Skitani, T., Zschieschang, U., Klauk, H., Someya, T. Flexible Organic Transistors and Circuits with Extreme Bending Stability. 2010.Nature Materials, vol. 9, pp. 1015-1022. (Year: 2010).

* cited by examiner

FLEXIBLE NEURAL PROBES

DOMESTIC PRIORITY

This application is a divisional of and claims priority from U.S. patent application Ser. No. 15/268,020, filed on Sep. 16, 2016, entitled "FLEXIBLE NEURAL PROBES" the entire contents of which are incorporated herein by reference.

BACKGROUND

The present invention relates generally to electrodes for studying neural activity, and more specifically to flexible active microelectrodes for studying neural activity.

Microelectrodes can be useful in recording and analyzing neuronal activity in brain tissue. Microelectrode arrays can contain multiple shanks that form an interface between neurons and electronic devices. Microelectrodes for use in such applications can be active or passive. Passive electrodes can include wiring and electronic probes, wherein the number of sensors is limited by wiring. Active electrodes include electrodes that have built in circuitry, and they can have greater density than passive electrodes.

SUMMARY

In accordance with one or more embodiments, a microelectrode includes a flexible shank. The flexible shank includes a flexible substrate. The flexible shank also includes a circuit. The flexible shank also includes a plurality of sensors. The microelectrode also includes a bioabsorbable material surrounding the flexible shank.

In accordance with another embodiment, a method of measuring neural activity includes embedding a flexible active electrode shank including a plurality of sensors in a bioabsorbable material. The method also includes implanting the flexible active electrode shank in a biological tissue. The method also includes sensing neural activity with the sensors.

In accordance with a further embodiment, a method of forming a flexible active electrode array includes depositing a flexible polymer on a substrate. The method also includes forming a plurality of sensors on the flexible polymer to create a flexible shank. The method also includes attaching a silicon-based chip to the flexible shank. The method also includes coating the flexible shank and the silicon-based chip in a bioabsorbable material. The method also includes cutting the flexible shank and the silicon-based chip and a portion of the bioabsorbable material from the substrate.

BRIEF DESCRIPTION OF THE DRAWINGS

The subject matter of embodiments of the invention is particularly pointed out and distinctly claimed in the claims at the conclusion of the specification. The foregoing and other features and advantages of the one or more embodiments described herein are apparent from the following detailed description taken in conjunction with the accompanying drawings in which:

FIGS. 4A, 4B, and 5-7 illustrate an exemplary method of forming a flexible active electrode array including a bioabsorbable material according to one or more embodiments, in which:

FIG. 4A illustrates a top-down view of exemplary active flexible electrode arrays after forming the arrays on a substrate;

FIG. 4B illustrates a cross-sectional side view of the exemplary electrode arrays formed on a substrate illustrated in FIG. 4A;

FIG. 5 illustrates a top-down view of exemplary electrode arrays after embedding the arrays in bioabsorbable material according to one or more embodiments;

FIG. 6 illustrates an exemplary electrode array after removing an array embedded in bioabsorbable material from the substrate;

FIG. 7 illustrates an exemplary electrode array after a portion of the bioabsorbable material is removed from the array.

DETAILED DESCRIPTION

Embodiments of the invention relate to flexible active neural microelectrodes and related methods of manufacture. The use of active electrodes in the study of neural activity is desirable. However, the sensitive tissues of the brain can be highly susceptible to damage upon insertion of a rigid material, such as those commonly used for active electrodes.

Passive electrodes can be used in the study of neural activity by insertion into the brain. Passive electrodes can include a number of sensors connected to flexible wires. Such electrodes can be sufficiently flexible to minimize damage to brain tissue, for example, upon movement of a patient due to respirator or cardiac cycles. However, the number of sensors can be limited by wiring as each probe can be associated with a wire.

Active electrodes can provide greater functionality in neurological applications, for instance, by multiplexing and amplifying the electrical current. However, conventional shanks for active electrodes include a rigid material, such as silicon, which can damage the neighboring tissue and have poor contact and, thus, reduced stability due to the lack of movement of the shank during respiratory or cardiac cycles.

Active electrodes can have improved density in comparison with passive electrodes and can have built in circuitry, making them desirable for a number of applications, including the study of neural activity. However conventional active electrode materials, for instance a TiN (titanium nitride) electrode with built in circuitry, are rigid resulting in damage to surrounding brain tissue. This rigidity can make such electrodes unsuitable for long-term studies and undesirable for short term studies.

The active electrodes described herein are be suitable for both short term and long term studies of neural activity. Flexible active electrodes can improve compliance between electrode and tissue and can minimize tissue damage. In one or more embodiments, flexible active electrodes are manufactured on a substrate, and then made suitably rigid for insertion into neural tissue by coating with a bio-dissolvable material. After dissolution of the rigid material upon insertion into the neural tissue, flexible active electrodes become sufficiently flexible to be suitable for short and long term studies of neural activity. Moreover, flexible active electrodes, according to one or more embodiments, have increased functionality or sensitivity in comparison with passive electrodes.

Figure 1:
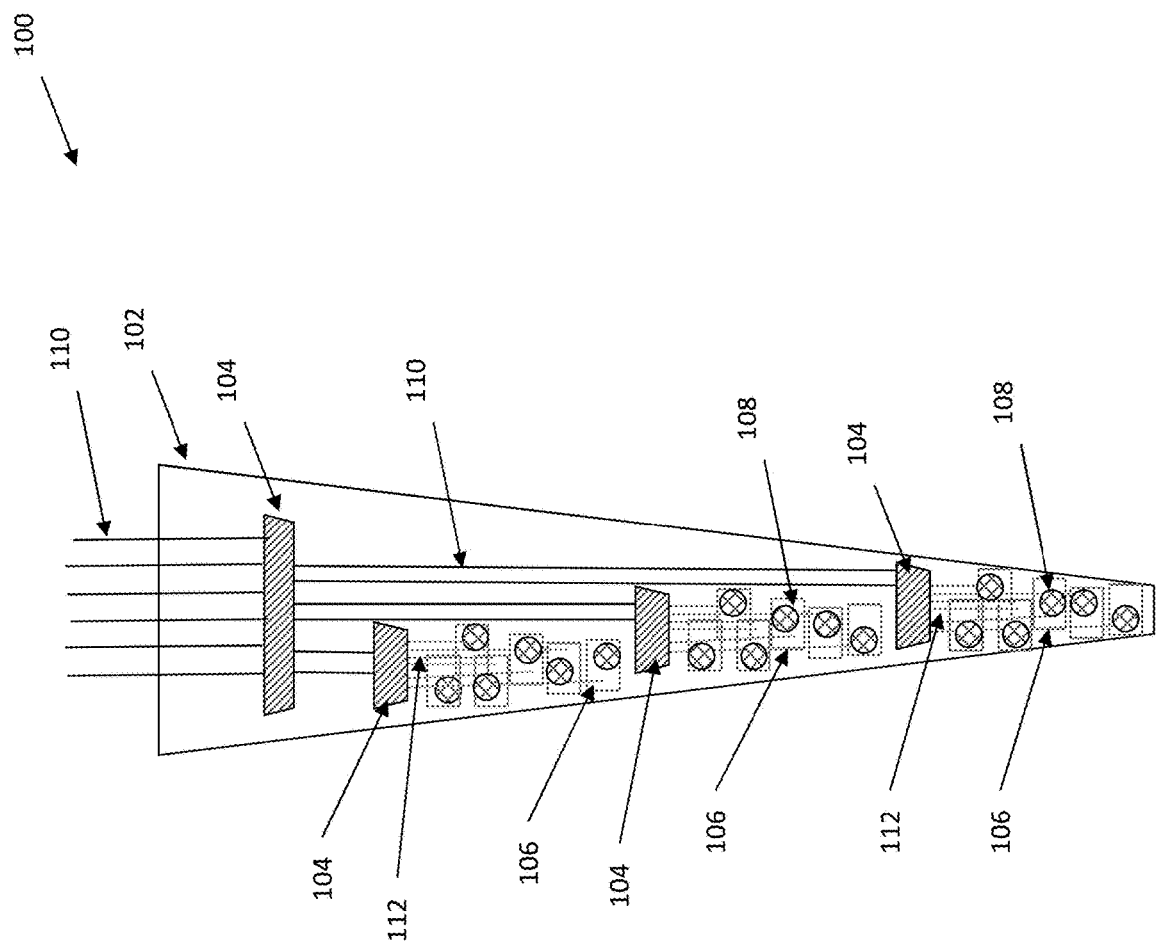
FIG. 1 illustrates an exemplary flexible active electrode shank according to one or more embodiments.

FIG. 1 illustrates an exemplary flexible active electrode shank 100 according to one or more embodiments. As is shown, the flexible active electrode shank 100 can include a flexible substrate 102. Within the flexible substrate 102 can be one or more circuits 104. The circuits can be connected to one another or to external components by a plurality of circuit wires 110. In some embodiments, each of the plurality of circuits 104 can be attached to another circuit 104 or to one or more sensor pixels 106 by way of a sensor wire 112. Sensor wires 112 and circuit wires 110 can be any conductive wire used in microelectronics and can be composed of the same materials or different materials. The sensor pixels 106 can contain a sensor or electrode 108.

Flexible substrate 102 can include a flexible polymeric material. For instance, the flexible substrate 102 can include, in some embodiments, polydimethylsiloxane (PDMS), polyimide (PI), polyurethane (PU), polymethylmethacrylate (PMMA), polyethylene terephthalate (PET), polystyrene, polycarbonate, polyvinyl alcohol (PVA), polybenzimidazole, polyester, and combinations thereof.

Circuits 104 can include any circuitry useful for detecting and processing neural activity. For example, and not by way of limitation, circuits 104 can include multiplexers (MUX) or demultiplexers (deMUX), signal conditioning circuits such as amplifiers and filters made by flexible electronics. For instance, in some embodiments, circuits can include metals, carbon nanotubes, graphene nanoribbons, or other related materials.

Sensor pixel 106 can include, in some embodiments, flexible complementary metal-oxide-semiconductor (CMOS) circuitry and can house a sensor or electrode 108. The CMOS circuits can include, for example, n-type field effect transistors (n-FETs) and p-type field effect transistors (p-FETs) fabricated with carbon nanotubes as channel materials. The sensor 108 or electrode can be any flexible sensor or electrode useful for studies of neural activity. Sensors 108 can include, for instance, metal, carbon nanotubes, graphene, or related materials.

Figure 2:
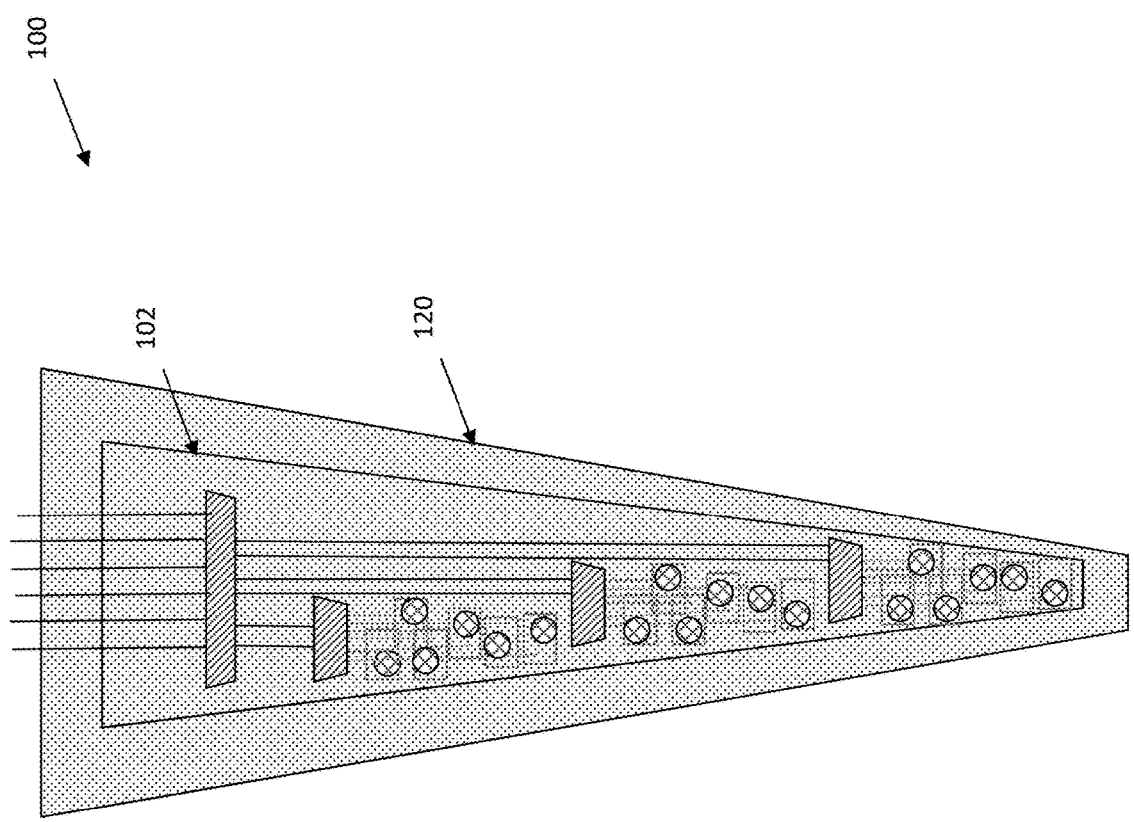
FIG. 2 illustrates an exemplary flexible active electrode shank embedded in bioabsorbable material according to one or more embodiments.

As is illustrated in FIG. 2, in some embodiments, the flexible shank 100 can be embedded in a bioabsorbable material 120. Bioabsorbable material 120 can by any material is sufficiently rigid to withstand stress accompanying implantation of the flexible shank, that can be safely administered to biological tissue and that can be absorbed, degraded, or softened by adjacent biological tissue. Exemplary bioabsorbable materials include, but are not limited to gelatin, polyglycolic acids (PGA), such as crystalline PGAs, and polylactic acids (PLA), including for instance poly-L-lactic acid (PLLA), poly-D-lactic acid, and amorphous PLA. In some embodiments, the bioabsorbable material 120 can dissolve after implantation, leaving a highly flexible active electrode. In some embodiments, the highly flexible active electrode can have high sensor density.

Figure 3:
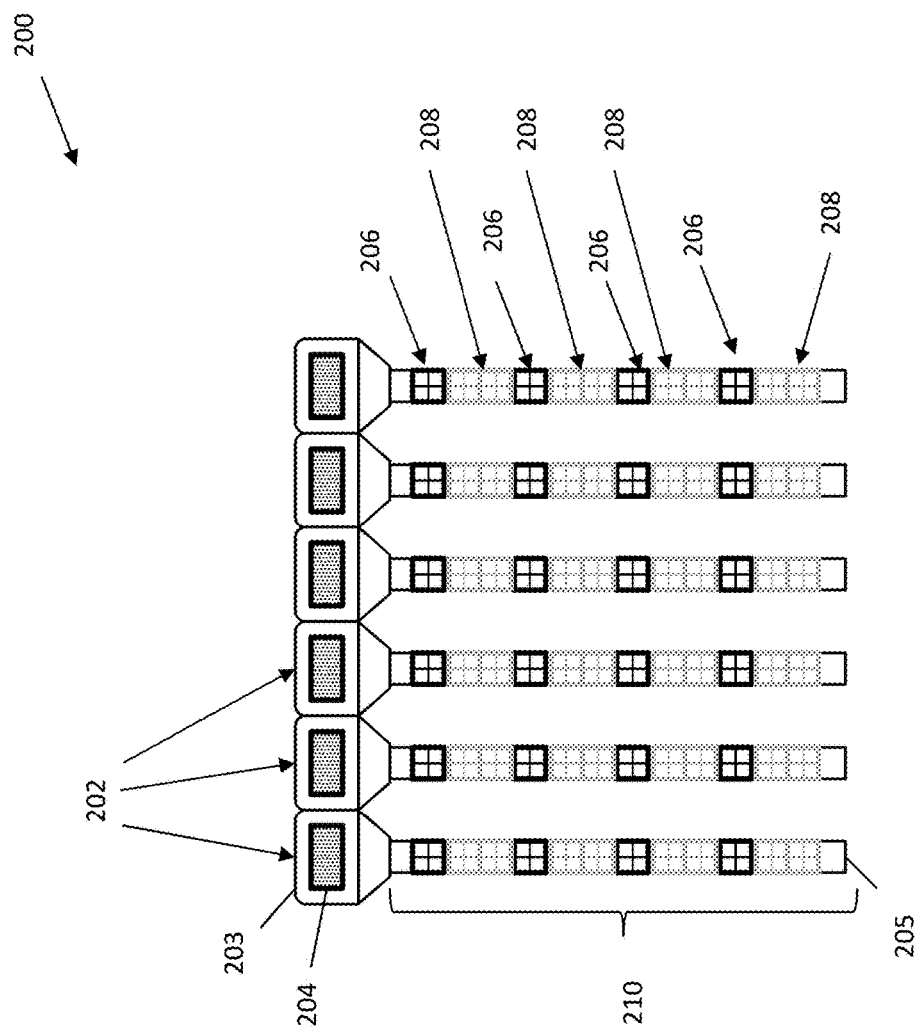
FIG. 3 illustrates an exemplary flexible active electrode array according to one or more embodiments.
Figures 4A, 4B:
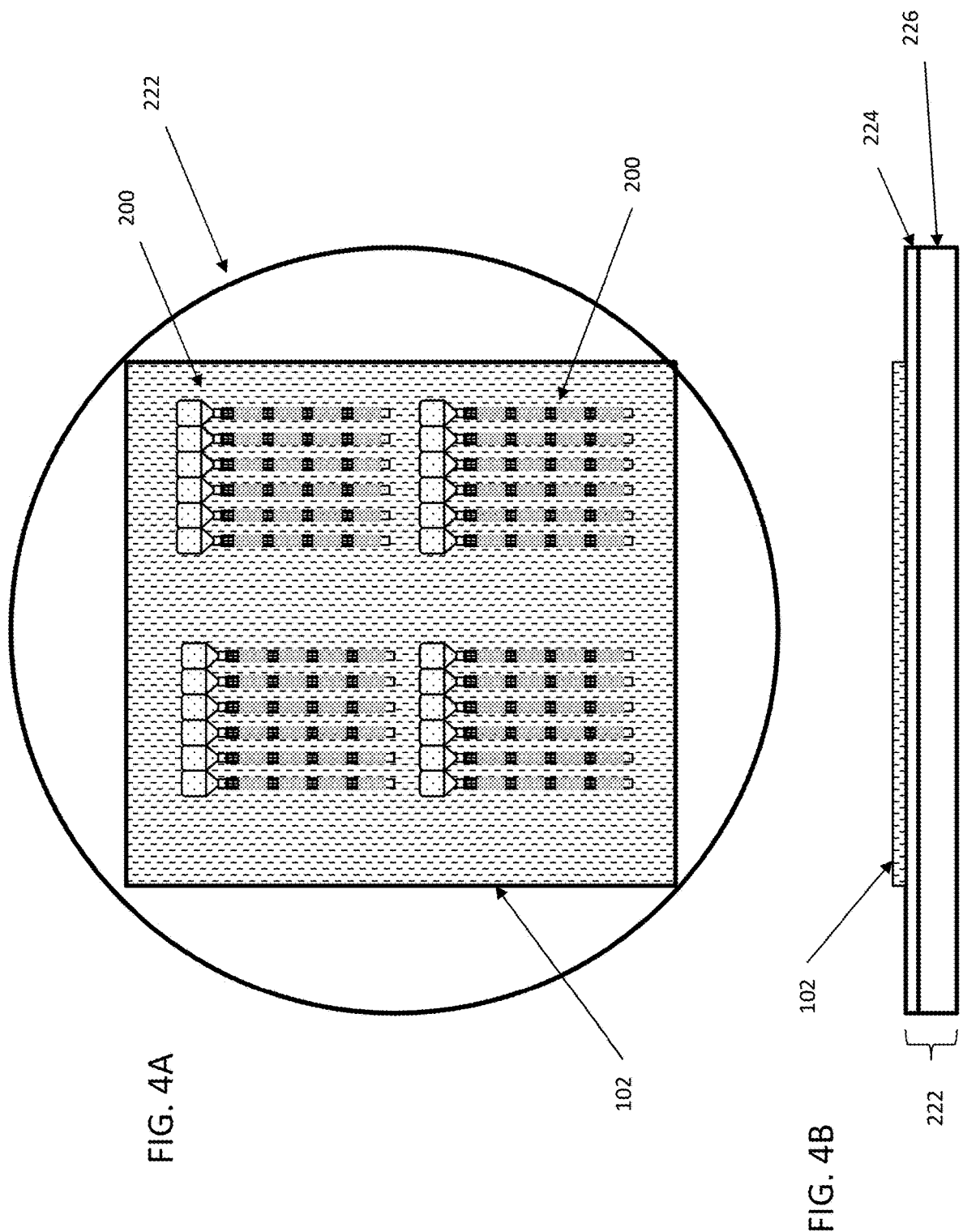

In some embodiments, a flexible shank can be part of an array. FIG. 3 illustrates an exemplary array of flexible active electrodes 200. The array 200 includes a plurality of electrode shanks 202, each shank having a top end 203 and a bottom end 205. The shanks 202 include a flexible polymer substrate 210 and a plurality of circuits, including routing circuits 206 and sensor circuits 208. Polymer substrate 210 includes a material such as those described for flexible substrate 102. In some embodiments, for instance, polymer substrate 210 includes PDMS or PI. In some embodiments, the polymer substrate 210 has a length of greater than or equal to 5 millimeters (mm) from the top end to the bottom end, such as from 5 mm to 10 mm. The polymer substrate 210 has a width, in some embodiments, of 50 to 75 micrometers (μm).

The routing circuits 206 include, in some embodiments, flexible circuits, such as flexible carbon nanotube circuits. The routing circuits 206 also include, in some embodiments, routing elements.

The sensor circuits 208 include, in some embodiments, flexible circuits, such as flexible carbon nanotube circuits. The sensor circuits 208 also include, in some embodiments, sensors. In some embodiments, the sensors include CMOS sensors having electrically isolated active regions. Preferably, a sensor circuit 208 is capable of receiving signals from and/or applying signals to neurons in one or more embodiments. In some embodiments, the sensor circuits 208 include a pH sensor. In some embodiments, the sensor circuits 208 include an action potential sensor. In some embodiments, the sensor circuits 208 include a local field potential (LFP) sensor. In some embodiments, the number of sensor circuits per shank is 10 to 50. In preferred embodiments, the number of sensor circuits per shank is 20 to 40, or 25 to 35, or 30 to 35.

In some embodiments, the array 200 includes an end chip 204, such as a CMOS end chip. The end chip 204 can be adjacent or near the top end 203 of the flexible shank. In some embodiments, every electrode shank 202 contains an end chip 204. In some embodiments, the end chip 204 is in communication with the sensor circuits 208 or routing circuits 206. In some embodiments, the end chip 204 is in communication with an external device (not shown).

In some embodiments, a flexible shank or an array is embedded in a bioabsorbable material, such as gelatin, for implantation into biological tissue. For example, the bioabsorbable material can impart sufficient rigidity to the flexible electrodes such that they can be inserted into the biological tissue. After insertion, the bioabsorbable material can lose its rigidity, by dissolution, absorption, or by other means, to minimize damage to the biological tissue during the course of study or investigation.

FIGS. 4 to 7 illustrate an exemplary method of forming a flexible active electrode array including a bioabsorbable material according to one or more embodiments. FIG. 4A illustrates a top-down view of exemplary active flexible electrode arrays 200 after forming the arrays 200 on a substrate 222. FIG. 4B illustrates a cross-sectional side view of the exemplary electrode arrays formed on a substrate illustrated in FIG. 4A. The substrate 222 can include, for example, a semiconductor material 226 and a sacrificial polymer layer 224. The semiconductor material 226 can be made of, for example, silicon (e.g., such as a silicon wafer), silicon germanium, or other suitable rigid supporting material. The sacrificial polymer layer 224 is used to release final fabricated flexible shanks from the supporting substrate 226. A flexible substrate 102 can be deposited on the substrate 222. Sensors and chips, such as CMOS end chips, and wiring of the arrays 200, as described above, can be fabricated according to known processes.

Figure 5:
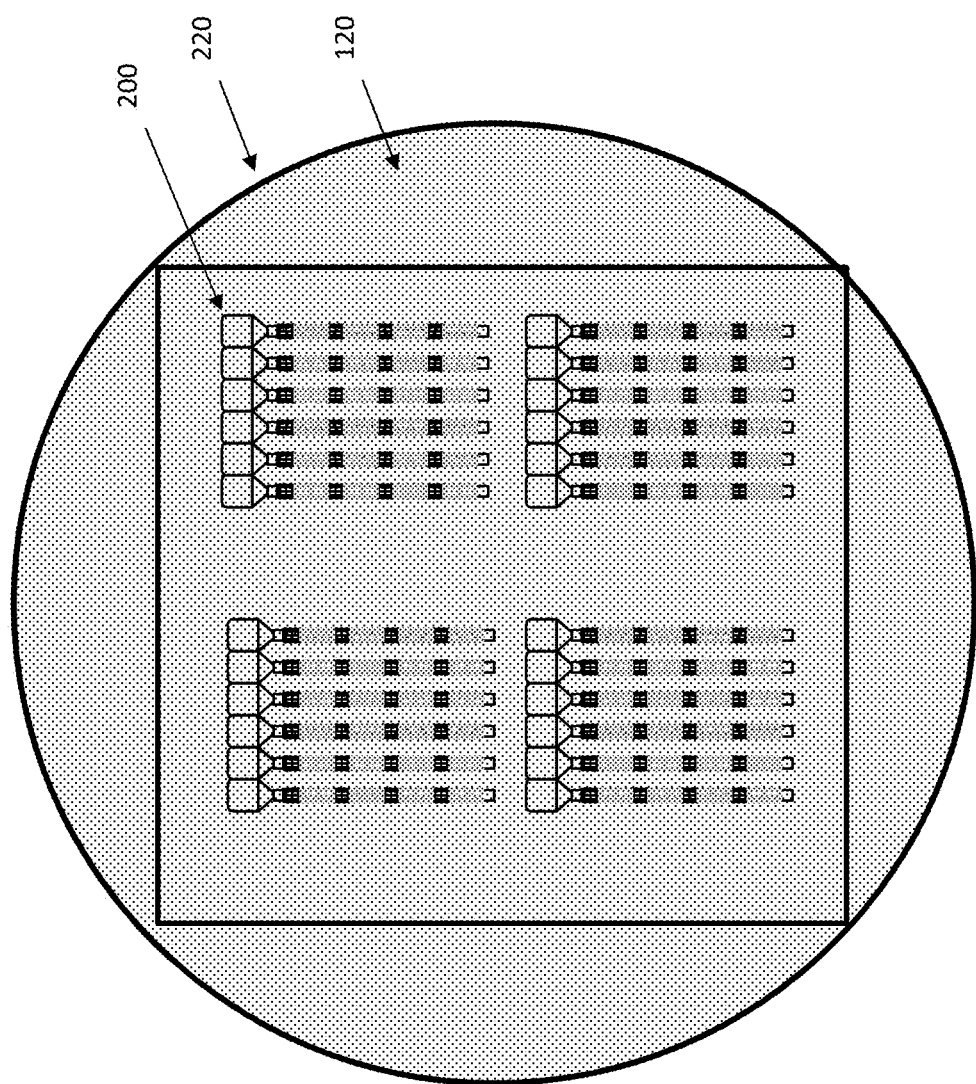

As is illustrated in FIG. 5, the active flexible electrode arrays 200 can be embedded in a bioabsorbable material 120 by coating the wafer 220 in a bioabsorbable material 120, such as gelatin.

Figure 6:
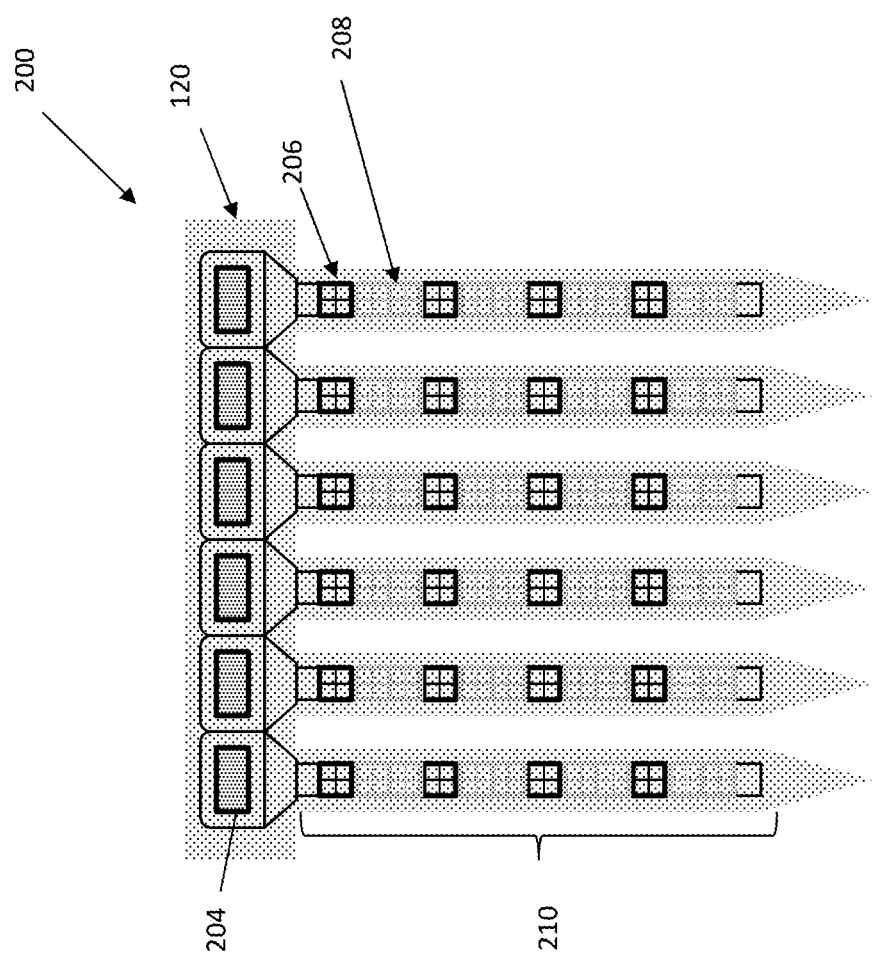

As is illustrated in FIG. 6, after coating the wafer 220 in a bioabsorbable material 120, an array 200 and adjacent bioabsorbable material 120 can be removed from the wafer. For example, in some embodiments, an array 200 is cut from the supporting wafer with laser milling. The bioabsorbable material 120 can surround the polymer substrate 210 and circuits 206, 208. In some embodiments, the bioabsorbable material 120 surrounds the end chips 204. In some embodiments, the bioabsorbable material 120 has a thickness of 15 to 20 μm and a width of 75 to 100 μm.

Figure 7:
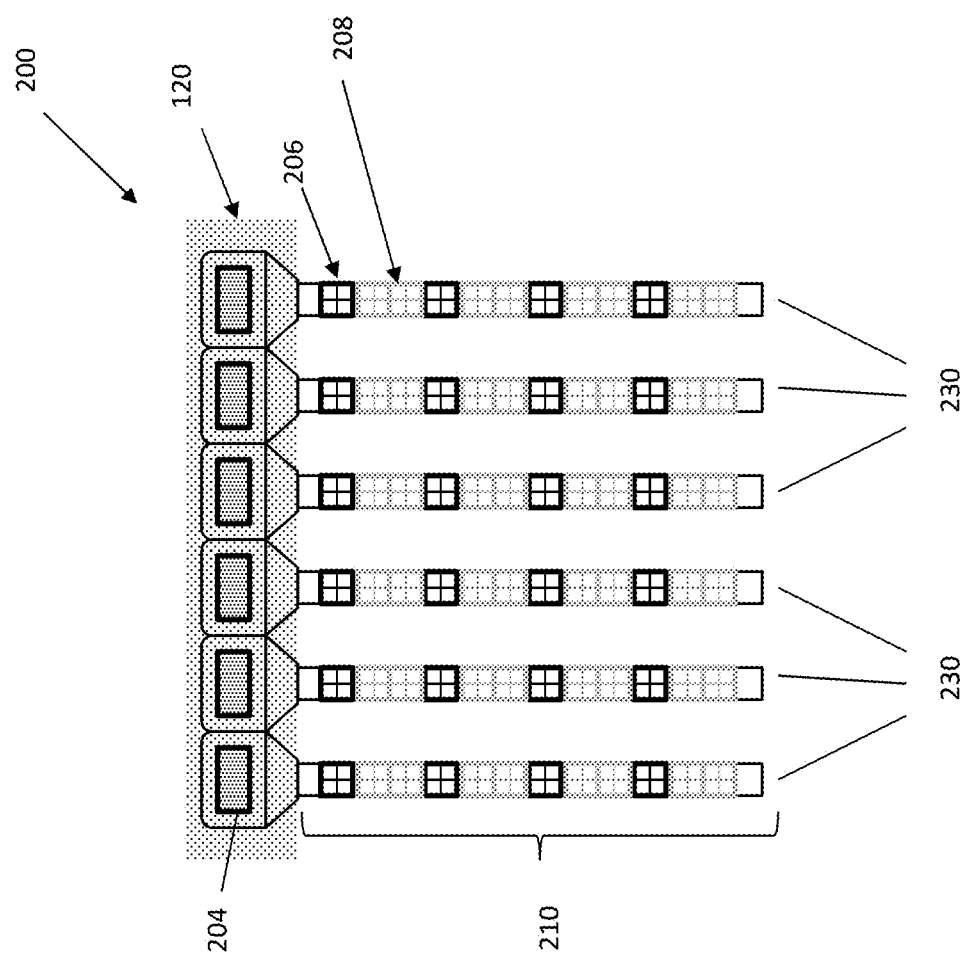

In some embodiments, an array and adjacent bioabsorbable material cut from the supporting wafer are inserted or implanted into biological tissue. After implanting an array into biological tissue, bioabsorbable material 120 can be removed from the polymer substrate 210 and sensors 206, 208, leaving active flexible electrode shanks 230, as are depicted in FIG. 7. In some embodiments, the bioabsorbable material is removed by absorption into surrounding biological tissue.

Figure 8:
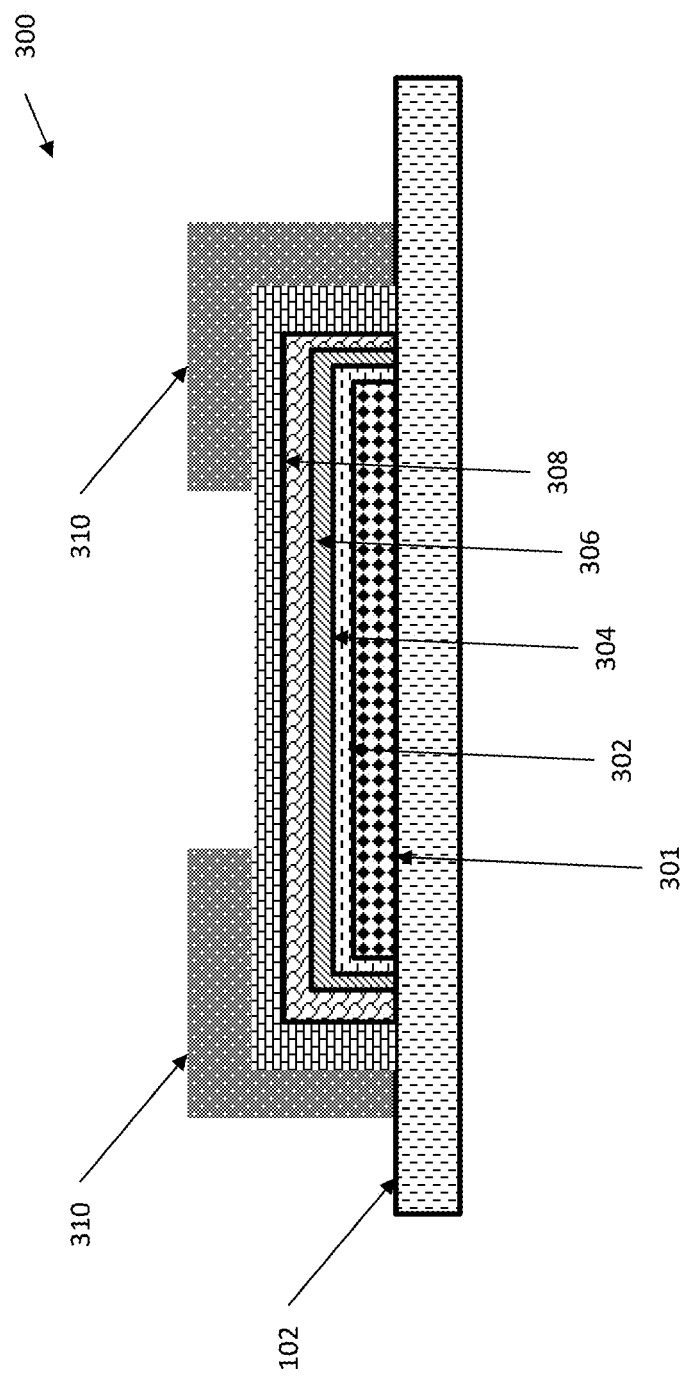
FIG. 8 illustrates an exemplary transistor on a flexible substrate according to one or more embodiments.

FIG. 8 illustrates an exemplary transistor 300 on a flexible substrate. As is shown, the transistor 300 can include a flexible substrate 102. The transistor 300 includes a work function metal in some embodiments. In some embodiments, the transistor 300 includes a low resistance metal.

In some embodiments, a first gate metal 301 can be deposited on the flexible substrate 102. First gate metal 301 can include, for example, a conductive metal such as gold.

In some embodiments, a second gate metal 302 can be deposited on the first gate metal 301. Second gate metal 302 can include a conductive metal such as titanium.

A gate dielectric 304 can be deposited on the second gate metal 302. In some embodiments, a layer of aminopropyltriethoxysilane (APTES) 306 and a carbon nanotube (CNT) layer 308, such as a CNT monolayer, can be deposited on the gate dielectric 304.

Electrodes 310 can be patterned on the transistor 300 and can include a source and drain region. In some embodiments, the source and drain can be high work-function material (e.g., palladium) for forming a p-type transistor. In some embodiments, the source and drain can be low work-function material (e.g., scandium) for forming an n-type transistor. Gate dielectric 304 can include, for example, a high-κ gate dielectric. Gate dielectric 304 includes, in some embodiments, an oxide material, such as aluminum oxide.

Figure 9:
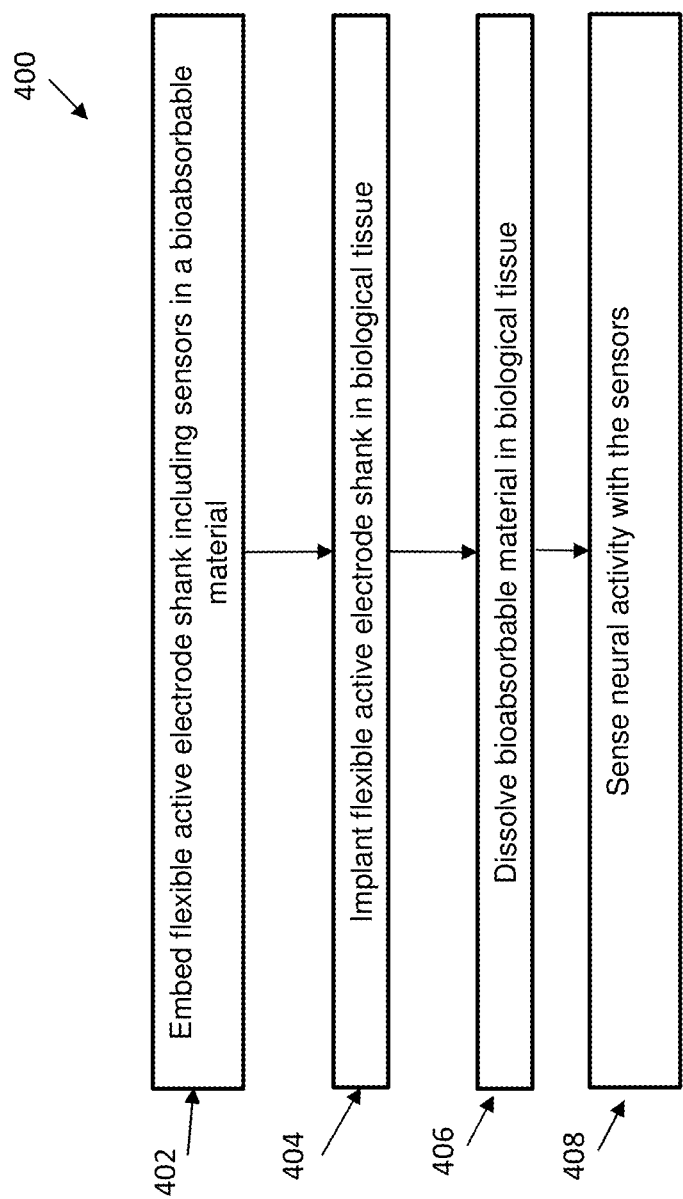
FIG. 9 is a flow diagram illustrating an exemplary method of measuring neural activity according to one or more embodiments.

Referring now to FIG. 9, a flow diagram of a method 400 for measuring neural activity in accordance with an exemplary embodiment is shown. As shown at block 402, the method 400 includes embedding a flexible active electrode shank including sensors in a bioabsorbable material. Next as shown at block 404, the method includes implanting flexible active electrode shanks in biological tissue. In some embodiments, the method 400 also includes, as shown at block 406, dissolving the bioabsorbable material in the biological tissue. Next, as shown at block 408, the method 400 includes sensing neural activity with the sensors.

In some embodiments, the method 400 also includes routing a signal received by the sensors, such as a neural signal (not shown). In some embodiments, the method 400 includes amplifying a signal received by the sensors (not shown). In some embodiments, the method 400 can include providing an output to the biological tissue, such as providing a signal to neural tissue (not shown).

Sensors can include electronic components capable of receiving a signal from biological tissue. Exemplary signals from biological tissue can include, but are not limited to, action potential, pH, or local field potential. Sensors can also include, in some embodiments, electronic components capable of providing an output to biological tissue or to other electronic components. In some embodiments, for example, sensors can include electrodes that provide an electrical signal to adjacent biological tissue.

Figure 10:
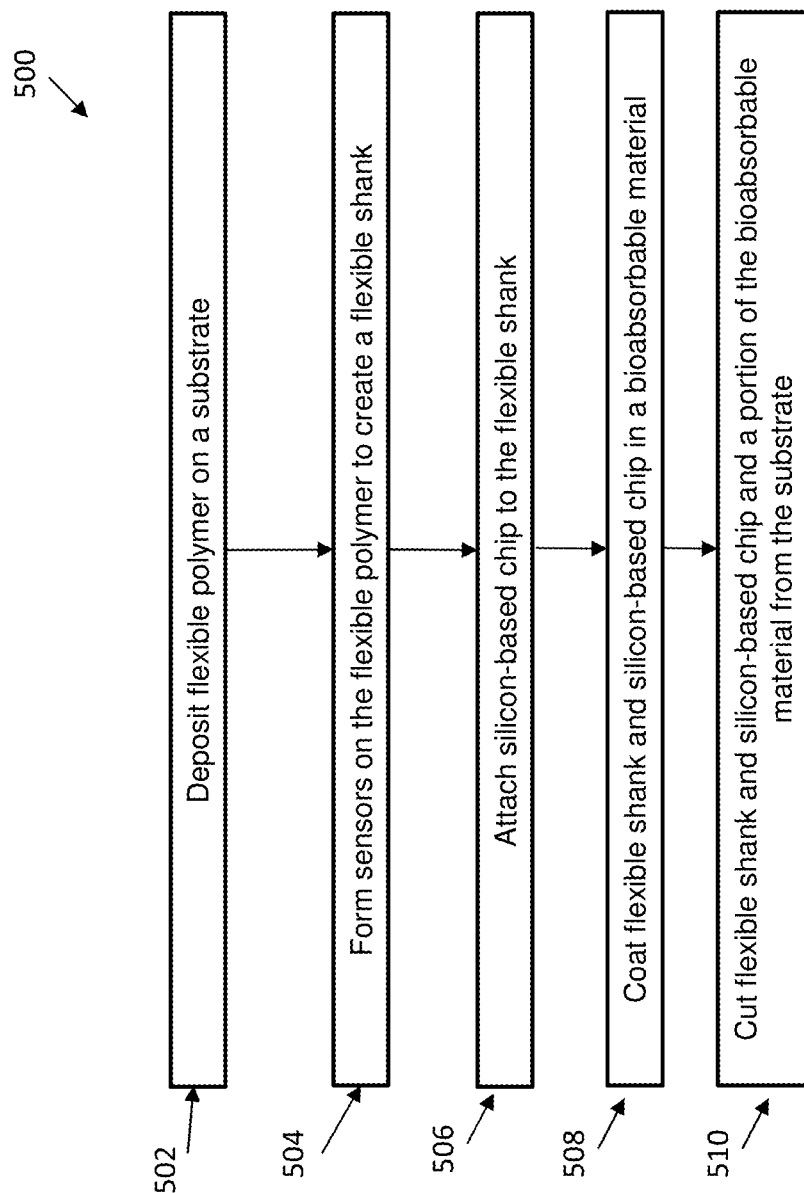
FIG. 10 is a flow diagram illustrating an exemplary method of forming a flexible active electrode array according to one or more embodiments.

Referring now to FIG. 10, a flow diagram of a method 500 for forming a flexible active electrode array in accordance with an exemplary embodiment is shown. As shown at block 502, the method 500 includes depositing a flexible polymer on a substrate. Next as shown at block 504, the method includes forming sensors on the flexible polymer to create a flexible shank. In some embodiments, the method 500 also includes, as shown at block 506, attaching a silicon-based chip to the flexible shank. Next, as shown at block 508, the method 500 includes coating the flexible shank and silicon-based chip in a bioabsorbable material. The method 500 also includes, as shown at block 510, cutting the flexible shank and silicon-based chip and a portion of the bioabsorbable material from the substrate.

In some embodiments, method 500 also includes laser milling the flexible shank, silicon-based chip, and a portion of the bioabsorbable material from the substrate (not shown).

In some embodiments, method 500 includes forming an array of flexible shanks and coating the array of flexible shanks in the bioabsorbable material (not shown). In some embodiments, method 500 includes cutting the array and a portion of the bioabsorbable material from the substrate, for example by laser milling (not shown).

Deposition is any process that grows, coats, or otherwise transfers a material onto the wafer. Available technologies include, but are not limited to, thermal oxidation, physical vapor deposition (PVD), chemical vapor deposition (CVD), electrochemical deposition (ECD), molecular beam epitaxy (MBE) and more recently, atomic layer deposition (ALD) among others.

Removal is any process that removes material from the wafer: examples include etch processes (either wet or dry), chemical-mechanical planarization (CMP), laser milling, etc.

Patterning is the shaping or altering of deposited materials, and is generally referred to as lithography. For example, in conventional lithography, the wafer is coated with a chemical called a photoresist; then, a machine called a stepper focuses, aligns, and moves a mask, exposing select portions of the wafer below to short wavelength light; the exposed regions are washed away by a developer solution. After etching or other processing, the remaining photoresist is removed. Patterning also includes electron-beam lithography, nanoimprint lithography, and reactive ion etching.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form described. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There can be many variations to this diagram or the steps (or operations) described therein without departing from the spirit of embodiments of the invention. For instance, the steps can be performed in a differing order or steps can be added, deleted or modified. All of these variations are considered a part of the claimed invention.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method of forming a flexible active electrode array, the method comprising:
   depositing a flexible polymer on a substrate;
   forming a plurality of sensors on the flexible polymer, the plurality of sensors configured into one or more arrays;
   attaching a silicon-based chip to an end of a first array of the one or more arrays;
   coating the first array and the silicon-based chip in a bioabsorbable material; and
   cutting the first array, the silicon-based chip, and a portion of the bioabsorbable material from the substrate to define a flexible shank.

2. The method of claim 1, wherein the cutting comprises laser milling.

3. The method of claim 1, wherein the bioabsorbable material comprises gelatin.

4. The method of claim 1 further comprising forming an array of flexible shanks.

5. The method of claim 1, wherein the plurality of sensors comprises a routing circuit.

6. The method of claim 1, wherein the plurality of sensors comprises an action potential sensor.

7. The method of claim 1 comprising forming greater than or equal to 25 sensors on the flexible polymer.

8. The method of claim 1 comprising forming greater than or equal to 30 sensors on the flexible polymer.

9. The method of claim 1 comprising forming a multiplexer on the flexible polymer.

10. The method of claim 1 comprising forming a demultiplexer on the flexible polymer.

11. The method of claim 1, wherein the plurality of sensors comprise carbon nanotubes.

12. The method of claim 1, wherein the plurality of sensors comprise graphene.

13. The method of claim 1, wherein the flexible polymer comprises polydimethylsiloxane.

14. The method of claim 1, wherein the plurality of sensors comprise complementary metal-oxide-semiconductor circuitry.

15. The method of claim 1 further comprising forming an electrode on the flexible polymer.

* * * * *